United States Patent [19]

White

[11] 4,307,188

[45] Dec. 22, 1981

[54] PRECURSOR INDICATOR COMPOSITIONS

[75] Inventor: William I. White, Elkhart, Ind.

[73] Assignee: Miles Laboratories, Inc., Elkhart, Ind.

[21] Appl. No.: 73,098

[22] Filed: Sep. 6, 1979

[51] Int. Cl.³ .................. C12Q 1/00; C12Q 1/48; C12Q 1/34; C12Q 1/44
[52] U.S. Cl. .................................. 435/4; 435/15; 435/18; 435/19; 435/21; 435/23; 435/24; 435/28; 435/805; 23/230 B
[58] Field of Search ................. 435/4, 15, 18, 19, 17, 435/16, 20, 21, 23, 24, 25, 28, 805, 810; 424/2; 23/230 B, 230 R

[56] References Cited

U.S. PATENT DOCUMENTS

| Re. 29,498 | 12/1977 | Meiattini | 435/14 |
| 4,119,405 | 10/1978 | Lam | 435/28 |
| 4,129,417 | 12/1978 | White | 435/18 |

OTHER PUBLICATIONS

Bergmeyer, "Determination of Concentration of Metabolites (End-Point Methods)", *Methods of Enzymatic Analysis*, vol. 1, Academic Press, N.Y., (1974), pp. 103–120.

*Primary Examiner*—Thomas G. Wiseman
*Attorney, Agent, or Firm*—Charles J. Herron

[57] ABSTRACT

A composition, test device, method of making a test device and process for determination of an analyte in a liquid sample are disclosed. More particularly, there is provided a composition for detecting an analyte in a liquid sample comprising an analyte-responsive component and an indicator composition having a plurality of components comprising at least one nonresponsive precursor component and at least one component effective in a liquid milieu to alter said precursor component so as to release at least one substance effective to permit said indicator composition, in combination with said analyte-responsive component, to produce a detectable response to said analyte. The composition can optionally be incorporated with a carrier to form a device.

27 Claims, No Drawings

PRECURSOR INDICATOR COMPOSITIONS

BACKGROUND OF THE INVENTION

1. Field of the Invention

The present invention relates generally to the field of diagnostic tests and, more particularly, to a precursor indicator composition for detecting an analyte.

2. Description of the Prior Art

The prior art has developed a wide variety of test compositions for the determination of specific constituents in liquids such as urine and blood. These have taken a variety of forms, one of the most popular being reagent impregnated test strips of the dip-and-read type, certain of which are useful for the determination of such constituents as glucose, protein, occult blood, and the like in body fluids, whereas others are useful for the determination of various constituents in other liquids, such as swimming pool water, cutting fluids, and the like.

Many current methods require the use of numerous labile ingredients. At present one of the greatest difficulties faced by diagnostic reagent manufacturers is the stability and shelf life of their product. Unreliable tests can result in the withholding of critical medical treatment, unnecessary treatment and lost income to the patient and the manufacturer. As a result many varied attempts have been made at overcoming this problem.

Compositions and test devices in the form of treated carrier matrices are often stored for considerable periods of time before use, and it is therefore desirable that the reagents chosen are not easily auto-oxidizable in air. It has generally been considered necessary that the test devices be protected from exposure to light and often it has been necessary to keep them sealed in a moisture repellent package which is opened only for removal of one or more test devices shortly before use.

In another approach, various stabilizer compounds have been added to analytical compositions. Exemplary of efforts in this approach are U.S. Pat. Nos. 3,551,296; 3,950,133; 4,118,279; and 4,132,598.

In the variety of approaches taken to enhance the stability of diagnostic compositions it has heretofore been considered necessary to add stabilizer compounds, which present the possibility of altering the reaction characteristics of the composition, or accepting that the composition is labile and providing otherwise unnecessary elaborate packaging to protect the composition.

It is therefore an object of the present invention to provide an improved test for the detection of an analyte, particularly in body fluids.

It is yet another object of the invention to provide an improved test for an analyte using materials which provide improved stability.

A further object of the invention is to provide an improved test for the detection of an analyte which undergoes alteration to an analyte responsive form when put in use.

SUMMARY OF THE INVENTION

In accordance with the present invention there are provided a composition, test device, method of making a test device and process for determination of an analyte in a liquid sample. More particularly, there is provided a composition for detecting an analyte in a liquid sample comprising an analyte-responsive component and an indicator composition having a plurality of components and comprising at least one nonresponsive precursor component and at least one component effective in a liquid milieu to alter said precursor component so as to release at least one substance effective to permit said indicator composition, in combination with said analyte-responsive component, to produce a detectable response to said analyte. The composition can optionally be incorporated with a carrier to form a device.

There are major advantages achieved by the composition according to the invention. First, the indicator precursor is more stable than the indicator itself. In the case of an oxidation indicator, for example, the precursor will be less subject to air oxidation or to oxidation from oxidizing agents in the same formulation. Also, in many cases, the precursor will be a solid where the indicator itself is a liquid. This would facilitate incorporation of the ingredient into a test device such as a strip or tablet. Additionally, it may be that the indicator itself is hazardous in some manner, while the precursor would be nonhazardous.

DESCRIPTION OF THE PREFERRED EMBODIMENTS

Specific terms used in the following description are intended to refer only to the particular embodiment selected for illustration and not to limit the invention.

In one embodiment the invention provides a composition comprising an analyte-responsive component and an indicator composition comprising a nonresponsive precursor component and a component effective in a liquid milieu to alter the precursor component so as to release an indicator compound which in combination with said analyte-responsive component produces a detectable response.

One example of this embodiment is a composition wherein the nonresponsive precursor component is indoxyl acetate and the component effective to alter said nonresponsive precursor component is a catalyst, such as an enzyme, capable of cleaving the acetate group from the indoxyl acetate. The component effective to alter said nonresponsive precursor component in this example is preferably cholinesterase.

In another example, the nonresponsive precursor component is a compound having the structure

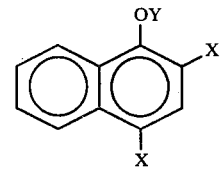

in which Y is lower alkyl carbonyl, lower alkoxy carbonyl or a phosphate ester of the structure

in which R and R' are independently H or lower alkyl, and, each X is bromine or chlorine and is independently selected. The term lower alkyl is intended to refer at least and preferably to $C_1$-$C_4$ alkyl. The component effective to alter said nonresponsive precursor component is an esterase when Y is alkyl carbonyl, a carbonic anhydrase when Y is lower alkoxy carbonyl or a phosphatase when Y is phosphate ester.

In still another example, the nonresponsive precursor component is a compound having the structure

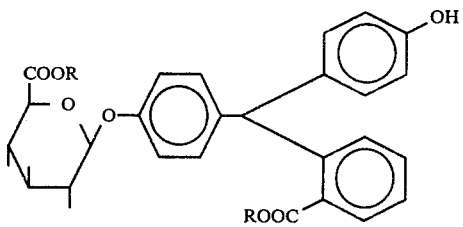

in which R is independently hydrogen or lower alkyl. The term lower alkyl is intended to refer at least and preferably to $C_1$-$C_4$ alkyl. The component effective to alter said nonresponsive precursor component is β-glucuronidase.

In another embodiment the composition includes an indicator which comprises a substance resulting from the alteration of the precursor component and an interreactive component.

In this embodiment, the interreactive component is a hydrazone, preferably selected from the group of 3-lower alkyl-2-benzothiazolinone hydrazone or 1-loweralkyl-2-quinolinone hydrazone.

The hydrazones are condensation products of a hydrazine with an aldehyde or ketone and contain the grouping =C=NNH$_2$. Many hydrazones are capable of oxidatively coupling with the contemplated examples of precursor component to form a colored entity. Such hydrazones include, among other, 3-methyl-2-benzothiazolinone hydrazone, 1-methyl-2-quinolinone hydrazone, N-methyl-pyridone-4-hydrazone, N-methyl-pyridone-2-hydrazone, 1-methyl-quinolinone-4-hydrazone, N-methyl-thiazolinone-2-hydrazone, N-methyl-oxazolinone-2-hydrazone, N-methyl-benzoxazolinone-2-hydrazone and 1,3-dimethylbenzimidazolinone-2-hydrazone. As used herein the expression "hydrazone" includes the acid addition salts thereof. Any conventional acid addition salt can be utilized such as those formed from hydrochloric acid, hydrobromic acid, sulfuric acid, nitric acid and the like. These acid addition salts can be used alone or they can be used in conjunction with the corresponding hydrazone.

In one example of this embodiment, the nonresponsive precursor component is (γ-glutamyl)-1-naphthylamine. The component effective to alter said nonresponsive precursor component is γ-glutamyl transferase.

In another example the nonresonsive precursor component is a lower peptide ester having the structure

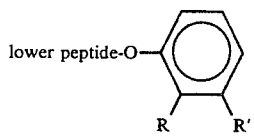

in which R and R' are independently hydrogen, alkyl, alkoxy, halogen, or together form an aromatc hydrocarbon ring. The term alkyl is intended to refer at least to $C_1$-$C_8$ alkyl. The component effective to alter said nonresponsive precursor component can be, for example, imidazole or an esterase.

In still another example the nonresponsive precursor component is a compound having the structure

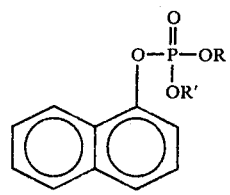

wherein R and R' are independently H or lower alkyl. The term lower alkyl is intended to refer at least and preferably to $C_1$-$C_4$ alkyl. The component effective to alter said nonresponsive precursor component is a phosphatase.

In an additional example the nonresponsive precursor component is a compound having the structure

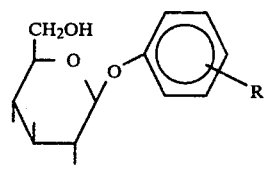

wherein R is H, lower alkyl, or lower alkoxy. The term lower alkyl is intended to refer at least and preferably to $C_1$-$C_4$ alkyl. The component effective to alter said nonresponsive precursor component is β-glucosidase.

Additionally, the nonresponsive precursor component can be, by way of example, a compound having the structure

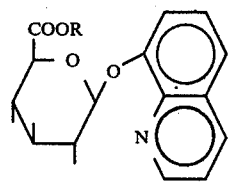

wherein R is H or lower alkyl. The term lower alkyl is intended to refer at least and preferably to $C_1$-$C_4$ alkyl. The component effective to alter said nonresponsive precursor component is β-glucuronidase.

In yet another embodiment the indicator comprises at least two nonresponsive precursor components and at least one component effective to alter the nonresponsive precursor components. Preferably there is at least one component effective specifically to alter each of said nonresponsive precursor components.

The composition according to the invention can take many physical forms and include many specific components regardless of the form assumed. These, along with known additives such as potentiating agents, which can additionally be employed if desired, are described. The test means is used to detect an analyte, particularly occult blood and glucose, by contacting it with a specimen such as urine, blood, serum, cerbrospinal fluid, tissue culture supernatant or the like.

In certain embodiments a dual enzyme system is present: one enzyme transforms the analyte to produce hydrogen peroxide, whereas the other enzyme has peroxidative activity. Substances having peroxidative activity which are useful in the present invention can be chosen from various well known organic and inorganic sources. Plant peroxidases, such as horseradish peroxidase or potato peroxidase, can be used. Inorganic compounds having peroxidase activity include iodides, such as sodium and ammonium iodides, and molybdates, such as potassium and ammonium molybdates. In addition, urohemin and a number of other porphyrin substances having peroxidative activity can be used. Other substances which are not enzymes, but which have peroxidative activity include such compounds as iron sulfocyanate, iron tannate, ferrous ferrocyanide, potassium chromic sulfate and the like.

The composition can be reconstituted for use as a solution for determination of the analyte. The solvents used in preparing the solutions can be water, physiological solutions, organic solvents, such as methanol, or mixtures thereof. It is preferably used to detect the analyte by contacting it with a specimen such as urine, cerebrospinal fluid, tissue culture supernatant serum or plasma.

When the composition is used in solution form, the analyte-responsive component is preferably used in concentrations of from about 1.0 mM (millimolar) to about 10 mM. The nonresponsive precursor is present in concentrations of from about 0.001 M to about 1.0 M and the component effective to alter the nonresponsive precursor is present in concentrations in relation to the concentration of the nonresponsive precursor. When peroxidase is present, concentrations thereof are preferably from about 0.001 milligram per milliliter (mg/ml) to about 1 mg/ml. The enzymes and other reagents in the examples can be obtained from Research Products Division, Miles Laboratories, Inc., Elkhart, Ind. or other commercial sources.

Likewise, there is provided a test device for the determination of an analyte which device comprises a carrier or matrix incorporated with the composition of the invention. The term carrier refers to matrices which are insoluble in and maintain their structural integrity when exposed to physiological or other liquid to be tested. Suitable matrices which can be used include paper, cellulose, wood, synthetic resin fleeces, glass fiber, nonwoven and woven fabrics, various organic polymers, such as polypropylene, and other organic materials well known as film formers to those skilled in the art. Elongated sheets of carrier material which have been incorporated with the composition of the invention are contemplated as devices as used herein. In manufacture and distribution these elongated sheets may take the form of bulk rolls, such as rolls of filter paper material. Alternatively, the carrier may take the form of a pressed or molded tablet containing conventional carrier material. For convenience, the carrier can be suitably attached to an insoluble support or handle member which can be made from polystyrene.

The device is prepared, for example, by impregnating a carrier with a solution of the composition of the invention and thereafter drying the impregnated carrier. Alternatively, it can be prepared by spraying, printing or incorporation of the composition with a known film forming polymer. The concentrations of reagents used in the dip range from about $10^{-3}$ mM up to a saturated solution. Peroxidase concentration is from about 0.01 mg/ml to about 20 mg/ml in the dip solution. The solvents used in preparing the impregnating solution can be water, physiological solutions, organic solvents or combinations thereof.

A process for the determination of the analyte in a fluid sample is provided which comprises contacting a sample with the composition or device according to the invention and observing any resultant color change. The test device is advantageously used by momentarily dipping it in a test sample or by otherwise introducing a test sample into the carrier matrix, whereby a detectable color change results when the analyte to be detected is present. The volumetric capacity of the carrier serves to limit the amount of sample absorbed thereby and to which the test means incorporated therewith is exposed. Any excess sample can be removed by washing or blotting the carrier to thereby limit the amount of sample tested to the volume thereof which has actually entered the carrier matrix. The test device can be used in the same way when sample of plasma, serum or other body fluids are tested.

Horseradish peroxidase and glucose oxidase used in the examples were obtained from Research Products Division, Miles Laboratories, Inc., Elkhart, Ind. A copolymer of methyl vinyl ether and maleic anhydride (Gantrez AN-139) and polyvinyl pyrrolidine (PVP) were obtained from GAF Corp., Chemical Products, N.Y., N.Y. The solvent used in preparing the solutions can be water, physiological solutions, organic solvents, such as methanol, or mixtures thereof.

The enzyme activity units (U) referred to in the Examples are defined as follows:

Peroxidase: that amount of enzyme producing 1 mg purpurogallin in 20 sec. at 20° C.
Alkaline Phosphatase: that amount of enzyme liberating 1 μmol phenol per minute from phenyl phosphate at 37° C.
Lipase: that amount of activity releasing 0.05 milliequivalents of fatty acid in 150 minutes at 30° C.
Glucose Oxidase: that amount of enzyme catalyzing the oxidation of 1 μmol β-D-Glucose per minute at 30° C.

The following Examples illustrate preferred embodiments of the invention.

EXAMPLE 1

In this example a comparison is made between protected and unprotected napthols used in a peroxide indicating detector system.

A 130 ml portion of distilled water was heated to 85° C. and 1.25 gram (g) Viscarin (Marine Colloids, Inc.) and 12.5 g Plasdone K29-31 polyvinyl pyrrolidone (GAF) were added. The solution was cooled to room temperature. Then, 12.5 ml ethanol and 104 ml 0.2 M glycine buffer (pH 9) were added. To this was added 75 ml of 5% solution of hydrolyzed Gantrez AN-139 (GAF) and 12.5 ml of a 10% solution of sodium lauroyl sarcosinate (Ciba-Geigy). To adjust the pH to 9.0, 4.5 ml 1 M sodium hydroxide was used. 15 ml 0.05 M $MgCl_2$ and 30 ml ethanol were added. To 124 ml of the solution was added 1.69 g horseradish peroxidase (Miles Laboratories, Inc., 110 1 U/mg).

Two 60 ml aliquots were taken. To the first was added 1.80 g alkaline phosphatase (Miles Laboratories, Inc., 5 U/mg) and the second was used without further additions. Two 4"×4" squares of filter paper (Eaton and Dikemann, No. 204) were dipped in each solution, and then dried in a forced-air oven at 40° C. for 20 minutes.

A second impregnation of each square was made in 25 ml of 0.02 M 3-methyl-2-benzothiazolinone hydrazone hydrochloride (MBTH) in water. A separate 25 ml solution was used for each piece of paper. The papers were dried in the same manner.

A third impregnation of each piece of paper was made in either 0.05 1 M 1-naphthol or 0.05 M 1-naphthylphosphate in methanol and dried in the same manner so as to give pieces of paper impregnated with the ingredients shown in Table 1:

TABLE 1

| Paper # | Ingredients |
|---|---|
| 1 | peroxidase, alkaline phosphatase, MBTH, 1-naphthylphosphate |
| 2 | peroxidase, alkaline phosphatase, MBTH, 1-naphthol |
| 3 | peroxidase, MBTH, 1-naphtholphosphate |
| 4 | peroxidase, MBTH, 1-naphthol |

Two small squares (1 cm × 1 cm) from each of these pieces of paper were cut out and placed on a nonabsorbent surface. On one small square was placed a drop of distilled water and on another was placed a drop of a solution prepared by taking a solution of commercially available hydrogen peroxide (Mallinkrodt) labeled 30% and diluting ½. Observations of color after such additions were recorded as in Table 2:

TABLE 2

| Paper # | Dry Paper | Water | $H_2O_2$ |
|---|---|---|---|
| 1 | white | white | red-brown |
| 2 | light brown | pink | red-brown |
| 3 | white | white | light green |
| 4 | pink | pink | red-brown |

It may be seen from the results with papers #2 and 4 that when naphthol alone is present as part of a peroxide detecting indicator system, it discolors even in the absence of the peroxide. When the nonresponsive indicator precursor component, naphthyl phosphate, is used no such premature discoloration is observed (papers 1 and 3). If there is no component effective to alter the precursor component as in the case of paper #3, then the desired reaction cannot take place even in the presence of peroxide. (The green color is due to radical species of MBTH which can sometimes be observed when there is no coupling component available with which it may react.) When the indicator precursor component and the component effective to alter the precursor component are both present, as in paper #1, then the performance is optimum.

EXAMPLE II

This example compares the stability of compositions including a protected and an unprotected napthol in another indicator system.

Three 4"×4" squares of Eaton and Dikeman #204 filter paper were impregnated and then dried after each impregnation for 20 minutes at 45° C. Solutions used in the impregnations are described in Table 3:

TABLE 3

| Paper # | First Impregnation | Second Impregnation |
|---|---|---|
| 1 | 9000 U/ml lipase (Miles triacylglycerol lipase, 600 U/ml) 2 mg/ml peroxidase (Miles, 110 U/mg) in 0.1 M phosphate buffer pH 6.4 | 0.05 M 1-naphthol in methanol |
| 2 | 9000 U/ml lipase (Miles, triacylglycerol lipase, 600 U/mg) 2 mg/ml peroxidase (Miles, 110 U/mg) in 0.1 M phosphate buffer pH 6.4 | 0.05 M 1-naphthyl laurate in methanol |
| 3 | 2 mg/ml peroxidase (Miles 110 U/mg) in 0.1 M phosphate buffer, pH 6.4 | 0.05 M 1-naphthyl laurate in methanol |

At first, papers #1 and 2 were both a light beige, due to impurities in the lipase, while paper #3 was white. After two days, paper #1 began to turn pinkish brown, while paper 2 remained light beige. This indicated that the unprotected naphthol was beginning to deteriorate, while the protected naphthyl phosphate was not.

Devices were prepared by cutting two 1 cm × 1 cm squares from each of the larger pieces. These devices were placed on a nonabsorbing surface. A drop of water was placed on each and, about 5 minutes later, a sample containing 0.27% hydrogen peroxide was added to one of the squares in each pair. The results observed were as set forth in Table 4:

TABLE 4

| Paper | Water | $H_2O_2$ |
|---|---|---|
| 1 | same as dry | purple |
| 2 | same as dry | purple |
| 3 | same as dry | same as dry |

Thus, it can be seen that the unprotected indicator deteriorates with time, while the indicator precursor does not. Further, if the component effective to alter the precursor component is absent, as in paper #3, the device fails to perform in detecting the presence of hydrogen peroxide.

EXAMPLE III

This example compares the stability of compositions including a protected and an unprotected napthol in an indicator system used for detecting the presence of glucose.

Three 4"×4" squares of Eaton and Dikeman #204 filter paper are impregnated and then dried after each impregnation for 20 minutes at 45° C. Solutions used in the impregnations are described in Table 5:

TABLE 5

| Paper # | First Impregnation | Second Impregnation |
|---|---|---|
| 1 | 9000 U/ml lipase (Miles triacylglycerol lipase 600 U/ml), 2 mg/ml peroxidase (Miles, 110 U/mg), 100 U/ml glucose oxidase (Miles, 1000 U/ml) in 0.1 M phosphate buffer pH 6.4 | 0.05 M 1-naphthol in methanol |
| 2 | 9000 U/ml lipase (Miles, triacylglycerol lipase, 600 U/mg) 2 mg/ml peroxidase (Miles, 110 U/mg) 100 U/ml glucose oxidase (Miles, 1000 U/ml) in 0.1 M phosphate buffer pH 6.4 | 0.05 M 1-naphthyl laurate in methanol |
| 3 | 2 mg/ml peroxidase (Miles 110 U/mg), 100 U/ml glucose oxidase (Miles, 1000 U/ml) in 0.1 M phosphate buffer, pH 6.4 | 0.05 M 1-naphthyl laurate in methanol |

At first, papers #1 and 2 are both a light beige, due to impurities in the lipase, while paper #3 is white. After two days, paper #1 begins to turn pinkish brown, while paper 2 remains light beige. This indicates that the unprotected naphthol is beginning to deteriorate, while the protected naphthyl phosphate is not.

Devices are prepared by cutting two 1 cm×1 cm squares from each of the larger pieces. These devices are placed on a nonabsorbing surface. A drop of water is placed on each and, about 5 minutes later, a sample containing 250 mg/ml glucose is added to one of the squares in each pair. The results obtained are as set forth in Table 6:

TABLE 6

| Paper | Water | Glucose |
|---|---|---|
| 1 | same as dry | purple |
| 2 | same as dry | purple |
| 3 | same as dry | same as dry |

Thus, it can be seen that the unprotected indicator deteriorates with time, while the indicator precursor does not. Further, if the component effective to alter the precursor component is absent, as in paper #3, the device fails to perform in detecting the presence of glucose.

EXAMPLE IV

The indicator system in this example uses a coupling of MBTH with naphthol to form a reddish colored azo dye.

In this example 4"×4" squares of Eaton and Dikeman #204 filter paper were impregnated and then dryed in a forced air oven for 20 minutes at 45° C. Solutions used in the impregnations were as described in Table 7:

TABLE 7

| Paper # | First Impregnation | Second Impregnation |
|---|---|---|
| 1 | 9000 U/ml lipase (Miles, triacylglycerol lipase, 600 U/mg) 2 mg/ml peroxidase (Miles, 110 U/mg) 0.1 M phosphate buffer pH 6.4 | 0.05 M 1-naphthyl-laurate and 0.02 M MBTH in methanol |
| 2 | 2 mg/ml peroxidase 0.1 M phosphate buffer, pH, 6.4 | 0.05 M 1-naphthyl-laurate and 0.02 M MBTH in methanol |
| 3 | 2 mg/ml peroxidase 0.1 M phosphate buffer, pH 6.4 | 0.05 M 1-naphthol and 0.02 M MBTH in methanol |

Paper #1 was a light beige due to lipase impurities. Paper #3 was pink due to either naphthol deterioration or premature coupling with the MBTH. Paper #2 was a very light yellow due to a slight deterioration of the MBTH; this slight deterioration of MBTH is believed to have occurred in the other papers as well, but the color was masked by the other colors on those papers. The pink color of paper #3 shows the instability of the unprotected indicator.

Devices were prepared by cutting two 1 cm×1 cm squares from the larger piece of each formula and placing these on a nonabsorbing surface. A drop of water was placed on each device, and about 5 minutes later, a sample containing 0.27% hydrogen peroxide was added to one of the devices in each pair. Results were as in Table 8:

TABLE 8

| Paper # | Water | $H_2O_2$ |
|---|---|---|
| 1 | same as dry | red-brown |
| 2 | same as dry | increase in yellow color |
| 3 | same as dry | red-brown |

Thus, it can be seen that the unprotected indicator coupler deteriorates to give a pink color on the device while the indicator precursor component does not. Further, if the agent for removing the protecting group is absent, as for devices prepared from paper #2, the device fails to perform in detecting the presence of hydrogen peroxide. The yellow color generated in devices prepared from paper #2 in the presence of hydrogen peroxide is from decomposition of MBTH which may take place when there is no coupling component with which it can react.

EXAMPLE V

This example reports the stability obtained in compositions using an indoxyl derivative.

Squares (4"×4") of Eaton and Dikeman #204 filter paper were impregnated and then dryed in a forced air oven for 20 minutes at 45° C. Solutions used in the impregnations were as described in Table 9:

TABLE 9

| Paper # | First Impregnation | Second Impregnation |
|---|---|---|
| 1 | 10 mg peroxidase, 0.2 M imidazole, in 10 ml 0.1 M phosphate buffer, pH 6.9 | 0.03 M indoxyl acetate in 5 ml benzene |
| 2 | 9 mg peroxidase in 10 ml 0.1 M phosphate buffer, pH 6.9 | 0.03 M indoxyl acetate in 5 ml benzene |

The papers were white when dry.

Devices were prepared by cutting two 1 cm×1 cm squares from papers of each formula and placing these on a nonabsorbing surface. A drop of water was placed on each device, and about 3 minutes later, a sample containing 0.27% hydrogen peroxide was added to one of the devices in each pair. Results were as in Table 10:

TABLE 10

| Paper # | Water | $H_2O_2$ |
|---|---|---|
| 1 | light blue after 15 minutes | blue-green after 15 minutes |
| 2 | white, blue on edges after 15 minutes | very light green after 15 minutes |

It can be seen that these devices are stable because a protecting indoxyl derivative is used rather than indoxyl itself. It is impossible to make formulations with indoxyl as the indicator because they turn blue immediately when contacted with air, forming indigo. When the imidazole is used as the component effective to alter the indicator precursor component, the difference between the presence and absence of hydrogen peroxide is readily detected by the much darker color with hydrogen peroxide, although a small amount of air oxidation occurs with water alone.

EXAMPLE VI

Devices were prepared as in Example V using 5-Bromoindoxyl acetate (Polysciences) instead of indoxyl acetate.

The devices were tested as in Example V with results of Table 11:

TABLE 11

| Paper # | Water | H₂O₂ |
|---|---|---|
| 1 | white with very light blue on edges | blue |
| 2 | white | white |

The same conclusions drawn from Example V are valid here.

EXAMPLE VII

Devices were prepared as in Example V using 5-bromo-4-chloroindoxyl acetate (Polysciences) instead of indoxyl acetate.

The devices were tested as in Example V with results in Table 12:

TABLE 12

| Paper # | Water | H₂O₂ |
|---|---|---|
| 1 | white with very light blue edges | blue green |
| 2 | white | light yellow |

The same conclusions drawn from Example V are valid here.

Although this invention has been described with a certain degree of particularity, numerous changes may be resorted to without departing from the scope of the invention.

What is claimed is:

1. A composition for detecting an analyte in a liquid sample comprising an analyte-responsive component and an indicator composition comprising (1) a nonresponsive precursor component having an ester or amide linkage and (2) a hydrolytic catalyst in an amount effective in a liquid milieu to cleave the ester or amide linkage so as to release a substance effective to permit said indicator composition, through reaction with a product of the analyte-responsive component, to produce a detectable response to the analyte.

2. The composition of claim 1 wherein the nonresponsive precursor component is indoxyl acetate and the component effective to alter said nonresponsive precursor component is a catalyst capable of cleaving the acetate group from the indoxyl acetate.

3. The composition of claim 2 wherein the component effective to alter said nonresponsive precursor component is cholinesterase.

4. The composition of claim 2 wherein the component effective to alter said nonresponsive precursor component is imidazole.

5. The composition of claim 1 wherein the nonresponsive precursor component is a compound having the structure

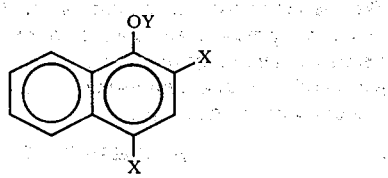

in which Y is lower alkyl carbonyl, lower alkoxy carbonyl or a phosphate ester of the structure

in which R and R' are independently H or lower alkyl, and, each X is independently selected from bromine and chlorine.

6. The composition of claim 5 wherein the component effective to alter said nonresponsive precursor component is an esterase when Y is alkyl carbonyl, a carbonic anhydrase when Y is lower alkoxy carbonyl or a phosphatase when Y is phosphate ester.

7. The composition of claim 1 wherein the nonresponsive precursor component is a compound having the structure

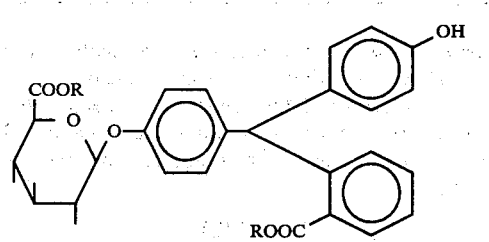

in which R is independently hydrogen or lower alkyl.

8. The composition of claim 7 wherein the component effective to alter said nonresponsive precursor component is β-glucuronidase.

9. The composition of claim 1 wherein the indicator comprises a component resulting from the alteration of the precursor component and an interreactive coupling compound selected from the group consisting of 3-loweralkykl-2-benzothiazolinone hydrazone and 1-loweralkyl-2-quinolinonehydrazone.

10. The composition of claim 9 wherein the nonresponsive precursor component is (γ-glutamyl)-1-naphthylamine.

11. The composition of claim 10 wherein the component effective to alter said nonresponsive precursor component is γ-glutamyl transferase.

12. The composition of claim 9 wherein the nonresponsive precursor component is a lower peptide ester having the structure

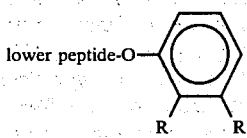

in which R and R' are independently hydrogen, alkyl, alkoxy, halogen, or together form an aromatic hydrocarbon ring.

13. The composition of claim 12 wherein the component effective to alter said nonresponsive precursor component is an esterase.

14. The composition of claim 9 wherein the nonresponsive precursor component is a component having the structure

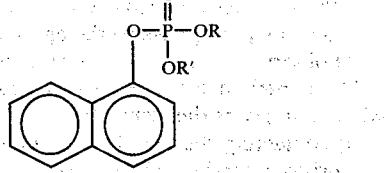

wherein R and R' are independently H or lower alkyl.

15. The composition of claim 14 wherein the component effective to alter said nonresponsive precursor component is a phosphatase.

16. The composition of claim 9 wherein the nonresponsive precursor component is a compound having the structure

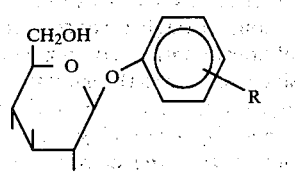

wherein R is H, lower alkyl, or lower alkoxy.

17. The composition of claim 16 wherein the component effective to alter said nonresponsive precursor component is β-glucosidase.

18. The composition of claim 9 wherein the nonresponsive precursor component is a compound having the structure

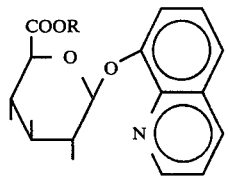

wherein R is H or lower alkyl.

19. The composition of claim 18 wherein the component effective to alter said nonresponsive precursor component is β-glucuronidase.

20. A device for detecting a sample analyte which comprises a carrier, which carrier is insoluble in and maintains its structural integrity when exposed to the sample to be tested, incorporated with a composition comprising an analyte-responsive component and an indicator composition comprising (1) a nonresponsive precursor component having an ester or amide linkage and (2) a hydrolytic catalyst in an amount effective in a liquid milieu to alter the nonresponsive precursor component so as to release a substance effective to permit the indicator composition, through reaction with a product of the analyte-responsive component, to produce a detectable response to the analyte.

21. A device for detecting a sample analyte which comprises a carrier, which carrier is insoluble in and maintains its structural integrity when exposed to the sample to be tested, incorporated with a composition comprising an analyte-responsive component and an indicator composition comprising (1) a nonresponsive precursor component having an ester or amide linkage; (2) a hydrolytic catalyst in an amount effective in a liquid milieu to alter the nonresponsive precursor component so as to release a substance effective to permit the indicator composition, through reaction with a product of the analyte-responsive component, to produce a detectable response to the analyte; (3) a component resulting from the alteration of the precursor component; and (4) a coupling compound, which is interreactive with the component resulting from the alteration of the precursor component and selected from the group consisting of 3-loweralkyl-2-benzothiazolinone hydrazone and 1-loweralkyl-2-quinolinone hydrazone.

22. A process for preparing a device for detecting a sample analyte which comprises the steps of:
(a) incorporating a carrier, which carrier is insoluble in and maintains its structural integrity when exposed to the sample to be tested, with a composition comprising an analyte-responsive component and an indicator composition comprising (1) a nonresponsive precursor component having an ester or amide linkage; (2) a hydrolytic catalyst in an amount effective in a liquid milieu to alter the nonresponsive precursor component so as to release a substance effective to permit the indicator composition, through reaction with a product of the analyte-responsive component, to produce a detectable response to the analyte; and thereafter
(b) drying the carrier which has been so incorporated.

23. A process for preparing a device for detecting a sample analyte which comprises the steps of:
(a) incorporating a carrier, which carrier is insoluble in and maintains its structural integrity when exposed to the sample to be tested, with a composition comprising an analyte-responsive component and an indicator composition comprising (1) a nonresponsive precursor component having an ester or amide linkage; (2) a hydrolytic catalyst in an amount effective in a liquid milieu to alter the nonresponsive precursor component so as to release a substance effective to permit the indicator composition, through reaction with a product of the analyte-responsive component, to produce a detectable response to the analyte; (3) a component resulting from the alteration of the precursor component; and (4) a coupling compound, which is interreactive with the component resulting from the alteration of the precursor component and selected from the group consisting of 3-loweralkyl-2-benzothiazolinone hydrazone and 1-loweralkyl-2-quinolinone hydrazone; and thereafter
(b) drying the carrier which has been so incorporated.

24. A method for detecting an analyte in a sample which comprises the steps of:
(a) contacting the sample with a composition comprising an analyte-responsive component and an indicator composition comprising (1) a nonresponsive precursor component having an ester or amide linkage and (2) a component effective in a liquid milieu to alter the nonresponsive precursor component so as to release a substance effective to permit the indicator composition, through reaction with a product of the analyte-responsive component, to produce a detectable response to the analyte; and thereafter
(b) observing any detectable response.

25. A method for detecting an analyte in a sample which comprises the steps of:

(a) contacting the sample with a composition comprising an analyte-responsive component and an indicator composition comprising (1) a nonresponsive precursor component having an ester or amide linkage and (2) a hydrolytic catalyst in an amount effective in a liquid milieu to alter the nonresponsive precursor component so as to release a substance effective to permit the indicator composition, through reaction with a product of the analyte-responsive component, to produce a detectable response to the analyte; (3) a component resulting from the alteration of the precursor component; and (4) a coupling compound, which is interreactive with the component resulting from the alteration of the precursor component and selected from the group consisting of 3-loweralkyl-2-benzothiazolinone hydrazone and 1-loweralkyl-2-quinolinone hydrazone; and thereafter (b) observing any detectable response.

26. A method for detecting an analyte in a sample which comprises the steps of:

(a) contacting the sample with a device which comprises a carrier, which carrier is insoluble in and maintains its structural integrity when exposed to the sample to be tested, incorporated with a composition comprising an analyte-responsive component and an indicator composition comprising (1) a nonresponsive precursor component having an ester or amide linkage and (2) a hydrolytic catalyst in an amount effective in a liquid milieu to alter the nonresponsive precursor component so as to release a substance effective to permit the indicator composition, through reaction with a product of the analyte-responsive component, to produce a detectable response to the analyte; and thereafter (b) observing any detectable response.

27. A method for detecting an analyte in a sample which comprises the steps of:

(a) contacting the sample with a device which comprises a carrier, which carrier is insoluble in and maintains its structural integrity when exposed to the sample to be tested, incorporated with a composition comprising an analyte-responsive component and an indicator composition comprising (1) a nonresponsive precursor component having an ester or amide linkage; (2) a hydrolytic catalyst in an amount effective in a liquid milieu to alter the nonresponsive precursor component so as to release a substance effective to permit the indicator composition, through reaction with a product of the analyte-responsive component, to produce a detectable response to the analyte; (3) a component resulting from the alteration of the precursor component; and (4) a coupling compound, which is interreactive with the component resulting from the alteration of the precursor component and selected from the group consisting of 3-loweralkyl-2-benzothiazolinone hydrazone and 1-loweralkyl-2-quinolinone hydrazone; and thereafter (b) observing any detectable response.

* * * * *